United States Patent
Fournier et al.

(10) Patent No.: US 9,771,618 B2
(45) Date of Patent: Sep. 26, 2017

(54) METHODS FOR TREATING BREAST CANCER

(75) Inventors: Marcia V. Fournier, Collegeville, PA (US); Katherine J. Martin, Belmont, MA (US)

(73) Assignee: Bioarray Genetics, Inc., Farmington, CT (US)

( * ) Notice: Subject to any disclaimer, the term of this patent is extended or adjusted under 35 U.S.C. 154(b) by 0 days.

(21) Appl. No.: 12/859,703

(22) Filed: Aug. 19, 2010

(65) Prior Publication Data

US 2011/0045480 A1     Feb. 24, 2011

Related U.S. Application Data

(60) Provisional application No. 61/235,139, filed on Aug. 19, 2009.

(51) Int. Cl.
*C12Q 1/68*     (2006.01)
*A01N 61/00*     (2006.01)

(52) U.S. Cl.
CPC .......... *C12Q 1/6886* (2013.01); *A01N 61/00* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,242,974 | A | 9/1993 | Holmes |
| 5,384,261 | A | 1/1995 | Winkler et al. |
| 5,405,783 | A | 4/1995 | Pirrung et al. |
| 5,412,087 | A | 5/1995 | McGall et al. |
| 5,424,186 | A | 6/1995 | Fodor et al. |
| 5,429,807 | A | 7/1995 | Matson et al. |
| 5,436,327 | A | 7/1995 | Southern et al. |
| 5,445,934 | A | 8/1995 | Fodor et al. |
| 5,472,672 | A | 12/1995 | Brennan |
| 5,527,681 | A | 6/1996 | Holmes |
| 5,529,756 | A | 6/1996 | Brennan |
| 5,532,128 | A | 7/1996 | Eggers et al. |
| 5,545,531 | A | 8/1996 | Rava et al. |
| 5,554,501 | A | 9/1996 | Coassin et al. |
| 5,556,752 | A | 9/1996 | Lockhart et al. |
| 5,561,071 | A | 10/1996 | Hollenberg et al. |
| 5,571,639 | A | 11/1996 | Hubbell et al. |
| 5,593,839 | A | 1/1997 | Hubbell et al. |
| 5,599,695 | A | 2/1997 | Pease et al. |
| 5,624,711 | A | 4/1997 | Sundberg et al. |
| 5,658,734 | A | 8/1997 | Brock et al. |
| 5,700,637 | A | 12/1997 | Southern |
| 6,004,755 | A | 12/1999 | Wang |
| 6,218,114 | B1 | 4/2001 | Peck et al. |
| 6,218,122 | B1 | 4/2001 | Friend et al. |
| 6,262,333 | B1 | 7/2001 | Endege et al. |
| 6,271,002 | B1 | 8/2001 | Linsley et al. |
| 2001/0051344 | A1 * | 12/2001 | Shalon et al. ............ 435/6 |
| 2008/0256011 | A1 | 10/2008 | Rice |
| 2009/0076734 | A1 | 3/2009 | Torres-Roca et al. |
| 2009/0093995 | A1 | 4/2009 | Woosley et al. |
| 2009/0105167 | A1 | 4/2009 | Potti et al. |
| 2009/0203533 | A1 | 8/2009 | Munnes et al. |
| 2009/0239214 | A1 | 9/2009 | Dai et al. |
| 2009/0239229 | A1 | 9/2009 | Weaver et al. |
| 2009/0275608 | A1 | 11/2009 | Ossovskaya et al. |
| 2010/0210738 | A1 | 8/2010 | Leyland-Jones et al. |
| 2013/0236567 | A1 | 9/2013 | Martin et al. |
| 2014/0162887 | A1 | 6/2014 | Martin et al. |

FOREIGN PATENT DOCUMENTS

| | | |
|---|---|---|
| EP | 2671067 | 12/2013 |
| WO | WO 2009/158143 A1 | 12/2009 |
| WO | WO 2011/130495 A1 | 10/2011 |
| WO | WO 2011/153545 A2 | 12/2011 |
| WO | WO 2012/106718 A1 | 8/2012 |

OTHER PUBLICATIONS

Enard et al, Science Apr. 12, 2002; 296(5566):340-43.*
Hoshikawa et al, Physiol. Genomics (2003) 12:209-219.*
Chan, Drug Discovery and Development, Apr. 2006, vol. 6 No. 3, pp. 1-6.*
Cheung et al Cold Spring Harbor Symposia Quant Biol (2003) vol. 68, pp. 403-407.*
Thisted University of Chicago (1998) pp. 1-5.*
Michiels et al. Lancet, 2005; 365:488-492.*
Slonin, Nature Genetics Supplement, vol. 32, Dec. 2002, pp. 502-508.*
Baker. Journal of the National Cancer Institute, vol. 95, No. 7, Apr. 2, 2003.*
Dunn et al. (Mol Diag Ther, 2009, 13(2), 73-90).*
Chen et al. "A Candidate Breast Tumor Suppressor and Biomarker for Tumor Progression" 2000 *Mol. Biol. Cell.* 11(4):1357-1367.
Allison "Biomarker-led adaptive trial blazes a trail in breast cancer" May, 2010, *Nature Biotechnology* 28(5):383-384.
Bonnefoi et al. "Predictive Signatures for Chemotherapy Sensitivity in Breast Cancer: Are They Ready for Use in the Clinic?" 2009, Eur. J. Cancer 45:17331743.
Fournier et al. "Gene Expression Signature in Organized and Growth-Arrested Mammary Acini Predicts Good Outcome in Breast Cancer" Jul. 15, 2006, Cancer Res. 66(14):7095-7102.
Gianni et al. "Gene Expression Profiles in Paraffin-Embedded Core Biopsy Tissue Predict Response to Chemotherapy in Women with Locally Advanced Breast Cancer" Oct. 10, 2005, J. Clin. Oncol. 23(29):7265-7277.
Hess et al. "Pharmacogenomic Predictor of Sensitivity to Preoperative Chemotherapy With Paclitaxel and Fluorouracil, Doxorubicin, and Cyclophosphamide in Breast Cancer" 2006, J. Clin. Oncol. 24:4236-4244.

(Continued)

*Primary Examiner* — Sarae Bausch
(74) *Attorney, Agent, or Firm* — Pepper Hamilton LLP

(57) ABSTRACT

Clinical tests for testing therapeutic sensitivity of cancerous breast tissue and methods and kits for performing the same are described herein. Embodiments of the present invention are directed to methods for predicting the efficacy of treatment of breast cancer. In addition, certain embodiments are directed to a kit for testing therapeutic sensitivity of breast cancer tissue.

10 Claims, 6 Drawing Sheets
(5 of 6 Drawing Sheet(s) Filed in Color)

(56) References Cited

OTHER PUBLICATIONS

Martin et al. "Predictive Value of a gene-signature identified in 3D Cultures in Breast Cancer Treated with Docetaxel or Paclitaxol/Fac" Apr. 2010, 2010 AACR Annual Meeting (presentation poster).
Martin et al. "Predictive value of a gene-signature identified in 3D cultures in breast cancer treated with Docetaxel" Apr. 19, 2009, 2009 AACR Annual Meeting (Denver, CO) Poster 32:10 (presentation abstract).
Martin et al. "Prognostic Breast Cancer Signature Identified from 3D Culture Model Accurately Predicts Clinical Outcome Across Independent Datasets" Aug. 2008, PLoS One 3(8):e2994.
Paik et al. "A Multigene Assay to Predict Recurrence of Tamoxifen-Treated, Node-Negative Breast Cancer" Dec. 30, 2004, *N. Engl. J. Med.* 351(27):2817-2826.
Parker et al. "Supervised Risk Predictor of Breast Cancer Based on Intrinsic Subtypes" Mar. 10, 2009, *J. Clin. Oncol.* 27(8):1160-1167.
Van De Vijver et al. "A Gene-Expression Signature as a Predictor of Survival in Breast Cancer" Dec. 19, 2002, *N. Engl. J. Med.* 347(25):1999-2009.
Fournier et al. "Transcriptome Profiling in Clinical Breast Cancer: From 3D Culture Models to Prognostic Signatures" 2006 J. Cell. Physiol. 209:625-630.
International Search Report dated Dec. 2, 2011 for PCT/US2011/39325.
Baker "The Central Role of Receiver Operating Characteristic (ROC) curves in Evaluating Tests for the Early Detection of Cancer" Apr. 2, 2003, J. National Cancer Inst. 95(7):511-515.
Chan "Integrating Transcriptomics and Proteomics" Apr. 1, 2006, Drug Discovery & Development 68:1-6.
Cheung et al. "Genetics of Quantitative Variation in Human Gene Expression" 2003, Cold Springs Harbor Symposia Quant. Biol. 68:403-407.
Enard et al. "Intra- and Interspecific Variation in Primate Gene Expression Patterns" Apr. 12, 2002, Science 296:340-343.
Hoshikawa et al. "Hypoxia Induces Different Genes in the Lungs of Rats Compared with Mice" 2003, Physiol. Genomics 12:209-219.
International Search Report dated Sep. 26, 2012 for PCT/US2012/23997.
Michiels et al. "Prediction of Cancer Outcome With Microarrays: a Multiple Random Validation Strategy" Feb. 5, 2005, The Lancet 365:488-492.
Thisted "What is a P-value?" Jun. 8, 1998, University of Chicago pp. 1-5.
Slonim "From Patterns to Pathways: Gene Expression Data Analysis Comes of Age" Dec. 2002, Nature Genetics Supplement 32:502-508.
Altschul et al. "Basic Local Alignment Search Tool" 1990, *J. Mol. Biol.* 215(3):403-410.
Bonadonna "Primary Chemotherapy in Operable Breast Cancer: Eight-Year Experience at the Milan Cancer Institute" 1998, *J. Clin. Oncol.* 16:93-100.
Devereux et al. "A Comprehensive Set of Sequence Analysis Programs for the VAX" 1984, *Nucleic Acids Research* 12(1):387-395.
Dolittle "Computer Methods for Macromolecular Sequence Analysis" 1996, *Methods in Enzymology* 266:3-711.
Esserman et al. "Chemotherapy Response and Recurrence-Free Survival in Neoadjuvant Breast Cancer Depends on Biomarker Profiles: Results from the I-SPY 1 Trial (CALGB 15007/15012; ACRIN 6657)" 2012, *Breast Cancer Res. Treat.* 132:1049-1062.
Fisher et al. "Effect of Preoperative Chemotherapy on the Outcome of Women with Operable Breast Cancer" 1998, *J. Clin. Oncol.* 16(8):2672-2685.
Higgins et al. "CLUSTAL: a Package for Performing Multiple Sequence Alignment on a Microcomputer" 1988, Gene 73:237-244.
Kuerer et al. "Clinical Course of Breast Cancer Patients with Complete Pathologic Primary Tumour and Axillary Lymph Node Response to Doxorubicin-Based Neoadjuvant Chemotherapy" 1999, *J. Clin. Oncol.* 17:460-469.
Shpaer "Sequence Data Analysis Guidebook" 1997, *Methods Mol. Biol.* 70:173-187.
Tatiana et al. "BLAST 2 Sequences, a new tool for comparing protein and nucleotide sequences" 1999, *FEMS Microbiology Letters* 174:247-250.
Bos et al. "Genes That Mediate Breast Cancer Metastasis to the Brain" 2009, *Nature* 159:1005-1009.
Dressman et al. "Gene Expression Profiles of Multiple Breast Cancer Phenotypes and Response to Neoadjuvant Chemotherapy" Feb. 1, 2006, Clin. Cancer Res. 12(3):819-826.
Dagliyan et al. "Optimization Based Tumor Classification from Microarray Gene Expression Data" (Feb. 2011) PLOS ONE 6(2):e14579:1-10.
Hosmer et al. "The Importance of Assessing the Fit of Logistic Regression Models: A Case Study" (Dec. 1991) Am. J. Public Health 81(12):1630-1635.
Lucentini "Gene Association Studies Typically Wrong" (Dec. 20, 2004) The Scientist 18(24):20.
Whitehead et al. Variation in Tissue-Specific Gene Expression Among N atural Populations (2005) Genome Biology 6:R13.
Wu Analysing Gene Expression Data from DNA Microarrays to Identify Candidate Genes (2001) J. Pathol. 195:53-65.

\* cited by examiner

Fig. 1. Confusion matrix and common performance metrics calculated from it.

FIG. 6

METHODS FOR TREATING BREAST CANCER

CROSS REFERENCE

This application claims priority to U.S. Provisional Application No. 61/235,139 filed Aug. 19, 2009, which is herein incorporated by reference in its entirety.

GOVERNMENT INTERESTS

Not applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not Applicable

BRIEF SUMMARY OF THE INVENTION

Embodiments of the present invention are directed to methods for predicting the efficacy of treatment of breast cancer comprising analyzing an expression profile of marker genes from a cancerous breast tissue and predicting the efficacy of treatment if the expression profile from the cancerous breast tissue matches a predetermined expression profile that indicates a patient will respond to the treatment. In another embodiment, the method may further comprise developing an expression profile from the marker genes. In yet another embodiment, a method may further comprise generating a report indicating the likelihood of long-term survival with breast cancer recurrence in the patient.

In another embodiment, methods for predicting the efficacy of treatment of breast cancer comprise a chemotherapeutic agent, radiation and a combination thereof. In another embodiment, the chemotherapeutic agent comprises alkylating agents, antimetabolites, anthracyclines, anti-tumor inhibitors, topoisomerase I inhibitors, topoisomerase II inhibitors, corticosteroids and combinations thereof. In a preferred embodiment, the therapeutic agent is an anti-mitotic agent. In yet another embodiment, the anti-mitotic agent is a taxane. In yet another embodiment, chemotherapy is provided to the patients after gene expression profiling.

In yet another embodiment, a kit for testing therapeutic sensitivity of breast cancer tissue is disclosed. The kit may comprise a means for identifying the expression profile of a tissue sample having probes to a specific set of genes or proteins associated with the disease; and labels, reagents, and other materials or instructions for labeling and preparing reagents and other materials necessary to develop an expression profile of one or more marker genes.

In another embodiment, a clinical test for breast cancer comprising a means of detecting an expression pattern of one or more marker genes from diseased tissue of a patient is described, wherein the expression level of at least one of the one or more genes is modulated compared to normal tissue and other diseased tissue; and wherein the modulation of the at least one gene is indicative a diseased tissue that is sensitive to a specific therapeutic agent.

In yet another embodiment, a method of identifying a breast cancer patient who is likely to respond to a treatment for breast cancer is described. The method may comprise developing a genetic profile from marker genes from a breast tissue sample; and identifying a breast cancer patient as likely to respond to a treatment for breast cancer if the expression profile matches a predetermined expression profile that indicates that a patient will respond to the treatment.

In certain embodiments, the marker genes may comprise ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof.

BRIEF DESCRIPTION OF THE DRAWINGS

The patent or application file contains at least on drawing executed in color. Copies of this patent or patent application publication with color drawing(s) will be provided by the Office upon request and payment of the necessary fee. For a fuller understanding of the nature and advantages of the present invention, reference should be made to the following detailed description taken in connection with the accompanying drawings, in which:

FIG. 6 is an illustrative overview of receiver operating characteristic (ROC) analysis.

DETAILED DESCRIPTION

Figure 1:
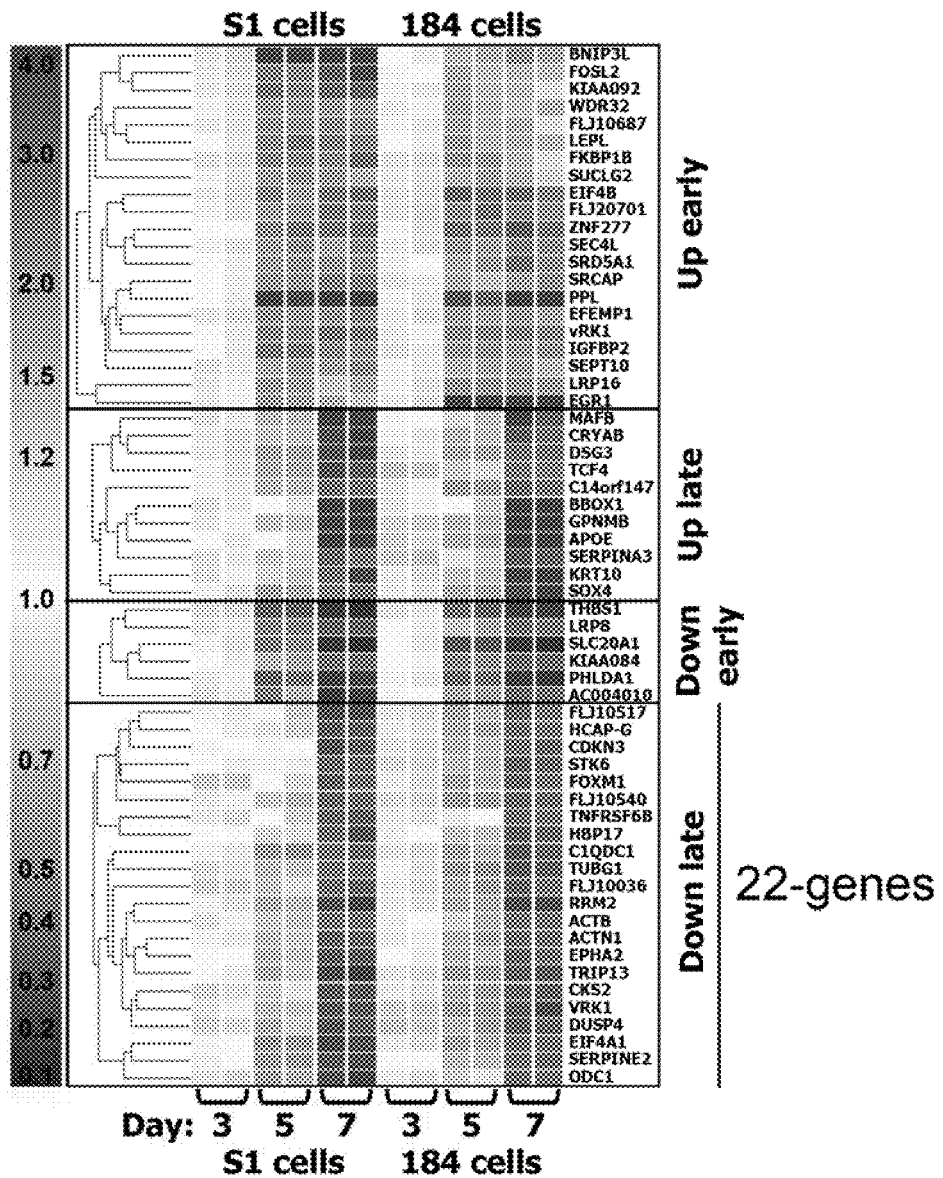
FIG. 1 shows the expression profile for two independently derived non-malignant human mammary epithelial cells (HMECs) HMT3522 S1 (S1) cells and 184 cells.

Before the compositions and methods provided herein are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. All publications mentioned herein are incorporated by reference in their entirety to the extent to support the present invention.

It must be noted that, as used herein and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral administration, injection, infusion, absorption or by any method in combination with other known techniques The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

Generally speaking, the term "tissue" refers to any aggregation of similarly specialized cells which are united in the performance of a particular function.

The term "improves" is used to convey that the present invention changes either the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of cancer are alleviated by administration of an active agent.

As used herein, the term "therapeutic" means an agent utilized to treat, combat, ameliorate, prevent or improve an unwanted condition or disease of a patient. In part, embodiments of the present invention are directed to predict the efficacy of cancer therapy by a 3D gene signature analysis. In certain embodiments, a therapeutic or therapeutic agent may be a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition.

The term "patient" generally refers to any living organism to which to compounds described herein are administered and may include, but is not limited to, any non-human mammal, primate or human. Such "patients" may or my not be exhibiting the signs, symptoms or pathology of the particular diseased state.

As used herein, a "kit" refers to one or more pharmaceutical compositions and instructions for administration or prescription of the one or more compositions. The instructions may consist of product insert, instructions on a package of one or more pharmaceutical compositions, or any other instruction.

As used herein, a "genetic profile" refers to a collection of information about an individual's DNA, RNA, protein, combinations of thereof or portions thereof. Portions of DNA, RNA or protein may provide important information regarding susceptibility to disease and responsiveness to treatment. Portions of DNA, RNA may include, but is not limited to, single nucleotide polymorphism, micro RNA, and combinations thereof. A portion of a protein is at least one amino acid or more from a protein that is indicated of susceptibility to disease and responsiveness to treatment.

Early detection of cancer is vital for patient survival by increasing treatment options. For example, breast cancer ranks as the second leading cause of death among women with cancer in the U.S., and early detection of breast cancer has a significant impact on patient survival, though a portion of patients still may relapse and may develop a more aggressive form of disease. As such, identifying a form of therapy that will be most effective for individuals with various types of cancer has become a primary focus of cancer research. Key steps include determining which patients will benefit from standard care therapies and assessing their chances of disease progression.

Metastasis is a multi-step process during which cancer cells disseminate from the site of primary tumors and establish secondary tumors in distant organs. While established cancer prognostic markers such as tumor size, grade, nodal, and hormone receptor status are useful in predicting survival in large populations, there is a need to develop better prognostic signatures to predict the efficacy of various forms of cancer treatment. A particular benefit would be the identification of patients with good prognoses whose tumors are highly unlikely to recur and who nevertheless are being treated with cytotoxic chemotherapies. The advent of gene expression technologies has greatly aided the identification of molecular signatures with value for tumor classification and prognosis prediction.

Embodiments of the present invention are directed to using a physiologically relevant model to identify a signature composed of key, biologically relevant genes that is likely to predict therapeutic efficacy across independent datasets. Candidate predictive genes were selected using a three dimensional (3D) cell culture model of non-malignant human cells that can reacquire the ability to form acini-like structures presenting a lumen, basal polarity and cell cycle arrest in laminin-rich extracellular matrix 3D cultures. These acinar structures replicate many of the characteristics of luminal cell differentiation in the mammary gland. The gene expression profiles of acini formation were determined as a function of time in culture. Gene expression that was modulated during growth arrest and acini formation in 3D cultures (3D-signature) was compared and validated against gene expression measured in cancer and then correlated to patient outcome.

Various embodiments of the invention are directed to clinical tests for therapeutic sensitivity by identifying a number of genes whose expression patterns are modified as a result of cancer, and other embodiments of the invention are directed to methods for performing such clinical tests. Still other embodiments of the invention are directed to kits which may include components necessary to perform such clinical tests for therapeutic sensitivity such as, for example, a means for aspirating cancerous cells from tumor or cancerous growth, components necessary to extract genetic material from aspirated cells, a means for tagging or labeling genetic material derived from the aspirated cells, a microarray having hybridization probes for a genetic signature, and a means for visualizing genetic material associated with the hybridization probes of the microarray.

The clinical test for therapeutic sensitivity of a disease may include a means for determining the expression levels of one or more genes from tissue exhibiting symptoms of a diseased state, and comparing these expression levels with those of normal healthy tissue or other diseased tissue samples and equating these expression levels with the efficacy of treatment for the diseased state. In certain embodiments, a report indicating the likelihood of long-term survival without breast cancer recurrence in a patient may be generated after the test. Determining the expression level for any one marker gene or set of marker genes such as those identified above and/or expression profile for any group or set of such genetic markers be carried out by any method and may vary among embodiments of the invention. For example, in some embodiments, the expression levels of one or more marker genes may be measured using polymerase chain reaction (PCR), enzyme-linked immunosorbent assay (ELISA), magnetic immunoassay (MIA), flow cytometry, and the like. In other embodiments, one or more microarray may be used to measure the expression level of one or more marker genes simultaneously. Various microarray types and configurations and methods for the production of such microarrays are known in the art and are described in, for example, U.S. Patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are hereby incorporated by reference in their entireties. Any such microarray may be useful in embodiments of the invention. For example, in some embodiments, antibodies raised against the protein product of the genetic marker may be used as probes in microarrays of the invention such that whole cell lysate or proteins isolated from cancerous cells may be passed over the microarray and expression levels of one or more genetic marker may be reduced based on the amount of protein captured by the microarray. In other embodiments, the expression level and/or expression profile for a specific genetic marker may be carried out by extracting cellular mRNA from cancerous cells and hybridizing the mRNA directly to single-stranded antisense DNA or RNA hybridization probes specifically targeted to the mRNA of the genetic marker. In certain embodiments, single-stranded antisense DNA or RNA hybridization probes may be used to capture copy DNA (cDNA) or copy RNA (cRNA) that was created from mRNA extracted from cancerous cells.

In particular embodiments, microarray analysis may involve the measurement of an intensity of a signal received from a labeled cDNA or cRNA derived from a sample obtained from cancerous tissue that hybridizes to a known nucleic acid sequence at a specific location on a microarray. In such embodiments, the hybridization probes used in the microarrays of the invention may be nucleic acid sequences that are capable of capturing labeled cDNA or cRNA produced from the mRNA of the marker gene. Typically, the intensity of the signal received may be proportional to the quantity of cDNA or cRNA, and thus the mRNA derived for the target gene in the cancerous tissue. Expression of the target gene may occur ordinarily in a healthy subject resulting in a base steady-state level of mRNA in normal tissue. However, in cancerous tissue, expression of the marker gene may be increased or decreased resulting in a higher level or lower level of mRNA, respectively, in diseased tissue. Alternatively, expression of a marker gene may not occur at detectable levels in normal, healthy tissue but occurs in cancerous tissue. The intensity measurements read from microarrays, as described above, may then be equated to the degree of expression of the gene corresponding to the signal intensity of labeled cDNA or cRNA captured by the hybridization probe. Thus, the microarrays of various embodiments of the invention may detect the variability in expression by detecting differences in mRNA levels in cancerous tissue over normal tissue or standard intensities and may be used to determine a particular course of treatment that may be most efficacious to the particular patient whose cancerous tissue is tested.

The clinical test of various embodiments may include a microarray having probes against one or more genes which may exhibit a modified expression pattern or profile as a result of cancer. Such genes may additionally be selected based on the likelihood that cells exhibiting the modified expression pattern or profile may be more likely to respond to a particular form of treatment. For example, in some embodiments, the hybridization probes provided on the microarray may have been selected based on the ability of one or more therapeutic agents to treat tumors exhibiting an expression profile associated with such hybridization probes. Therefore, by performing the clinical test, a clinician may predict the efficacy of the particular form of treatment based on the gene expression pattern or profile of cells extracted from a tumor as compared to normal, non-cancerous cells.

Embodiments of the invention are not limited based on the number of genes or the specific genes whose expression may be assessed or the type of treatment or therapeutic whose efficacy can be tested using the clinical test. For example, in some embodiments, the microarray may include probes for from 1 to greater than 500 genes whose expression patterns are modified in tumors or cancerous cells. In other embodiments, the microarray may include hybridization probes for from 2 to about 300, from about 5 to about 100, from about 10 to about 50, or from about 10 to about 25 genes. Without wishing to be bound by theory, microarrays including a larger number of hybridization probes such as, for example, 100 or more, 200 or more, 300 or more, or 500 or more may be capable to test for the efficacy of a greater number of therapeutic agents in a single test, whereas a microarray including a limited number of hybridization probes such as, for example, up to 5, up to 10, up to 15, up to 20, up to 25, up to 30, or up to 50, may be capable of more definitively testing the efficacy of a particular form of treatment. In particular embodiments, the microarray may include probes for from 15 to 30 genes such as 15, 16, 17, 18, 19, 20, 21, 22, 23, 24, 25, 26, 27, 28, 29, or 30 probes.

Similarly, the microarray may be prepared to test the expression level of any known gene or any gene that may be discovered that exhibits a change in expression in tumorigenic cells as compared to normal cells and which change in expression may be indicative of cells that respond to a specific form of treatment. In some embodiments, non-limiting examples of genes associated with various types of cancer, i.e., "genetic markers" or "marker genes", whose expression can be tested using the clinical tests and microarrays may include AC004010, ACTB, ACTN1, APOE, ASPM, AURKA, BBOX1, BIRC5, BLM, BM039, BNIP3L, C1QDC1, C14ORF147, CDC6, CDC45L, CDK3, CDKN3, CENPA, CEP55, CKS2, COL4A2, CRYAB, DC13, DSG3, DUSP4, EFEMP1, EGR1, EIF4A1, EIF4B, EPHA2, FEN1, FGFBP1, FKBP1B, FLJ10036, FLJ10517, FLJ10540, FLJ10687, FLJ20701, FOSL2, FOXM1, GPNMB, GSN, H2AFZ, HCAP-G, HBP17, HPV17, ID-GAP, IGFBP2, KIAA084, KIAA092, KNSL6, KNTC2, KRTC2, KRT10, LEPL, LEPR, LRP16, LRP8, LOC51203, LOC51659, LRP16, LRP8, MAFB, MCM6, MELK, M-RIP, MTB, NCAPG, NUSAP1, ODC, ODC1, PIG8, PHLDA1, PITRM1, PLK1, POLQ, PPL, PRC1, RAMP, RRM2, RRM3, SEC4L, SEPT10, SERPINE2, SERPINA3, SLC20A1, SMC4L1, SNRPA1, SOX4, SRCAP, SRD5A1, STK6, SUCLG2, SUPT16H, TCF4, THBS1, TNFRSF6B, TRIP13, TUBG1, UCHL5, VRK1, WDR32, ZNF227 and combinations thereof. In certain embodiments, the marker genes whose expression levels can be tested using the clinical test of various embodiments may be ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and any combinations thereof. The hybridization probes selected for the microarray may include any number and type of marker genes necessary to assure accurate and precise results, and in some embodiments, the number of hybridization probes may be economized to include, for example, a subset of genes whose expression profile is indicative of a particular type of cancer and/or treatment for which the microarray is designed to test.

Numerous techniques and methods are available for detecting intensity changes and making intensity measurements from microarrays to determine gene expression levels including, for example, the methods found in U.S. Pat. Nos. 6,271,002; 6,218,122; 6,218,114; and 6,004,755, the disclosure of each of which are hereby incorporated by reference in their entireties. In some embodiments, expression levels of one or more genetic markers may be conducted by comparing the intensity measurements derived from the microarrays. For example, in some embodiments, intensity measurement comparisons may be used to generate a ratio matrix of the expression intensities of genes in a test sample taken from cancerous tissue versus those in a control sample from normal tissue of the same type or of a previously collected sample of diseased tissue. The ratio of these expression intensities may indicate a change in gene expression between the test and control samples and may be used to determine, for example, the progression of the cancer, the likelihood that a particular form of therapy will be effective, and/or the effect a particular form of treatment has had on the patient.

In various embodiments, modulated genes may be defined as those genes that are differentially expressed in cancerous tissue as being either up regulated or down regulated. Up regulation and down regulation are relative terms meaning that a detectable difference, beyond the contribution of noise in the system used to measure it, may be found in the amount of expression of genes relative to some baseline. In such embodiments, a baseline expression level may be the measured from the amount of mRNA for a particular genetic marker in a normal cell. The one or more genetic markers in the cancerous tissue may be either up regulated or down regulated relative to the baseline level using the same measurement method. Distinctions between expression of a genetic marker in healthy tissue versus cancerous tissue may be made through the use of mathematical/statistical values that are related to each other. For example, in some embodiments, distinctions may be derived from a mean signal indicative of gene expression in normal, healthy tissue and variation from this mean signal may be interpreted as being indicative of cancerous tissue. In other embodiments, distinctions may be made by use of the mean signal ratios between different groups of readings, i.e. intensity measurements, and the standard deviations of the signal ratio measurements. A great number of such mathematical/statistical values can be used in their place such as return at a given percentile.

By determining the expression levels of genes that exhibit modulated expression in diseased, or cancerous tissue, a expression profile or genetic signature for particular diseased states may be determined, and because the expression profile for various disease types and various patients may vary, patients who are more likely to respond to specific types of therapy can be identified. For example, in some embodiments, the clinical tests of the invention may include a microarray configured to identify patients who will respond to a specific form of therapy based on their particular genetic profile. As such, the microarray may include a set of genes specifically associated with the diseased state. For example, in some embodiments, the microarray of the clinical test may include a set of 10-30 genes associated with cancer, and in some embodiments, the cancer tested using such clinical tests may be breast cancer.

Figure 4:
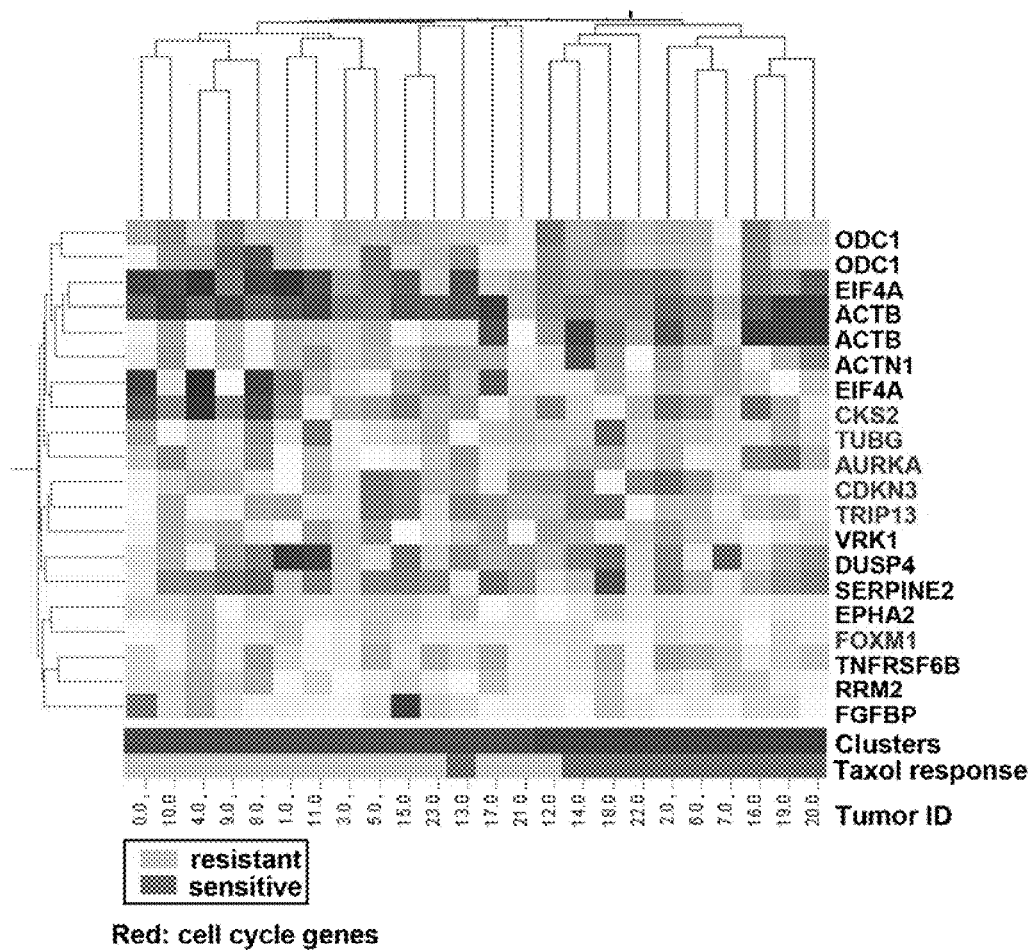
FIG. 4 shows the expression profile for the 22-gene signature for breast cancer patients.
Figure 5:
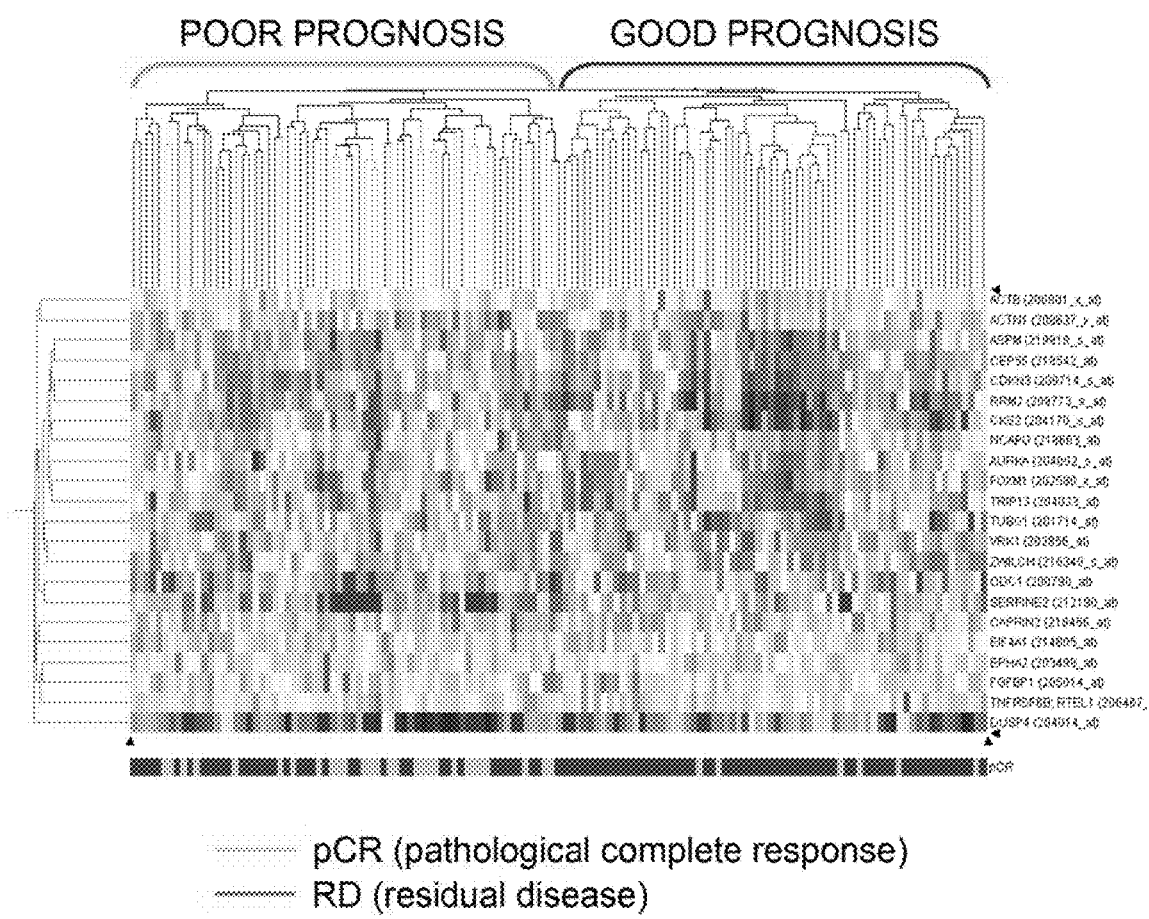
FIG. 5 shows the expression profile for the 22-gene signature for breast cancer patients.

In particular embodiments, a clinical test for breast cancer, the microarray may include probes for ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof. Table 1 depicts the gene symbol, aliases, description and the Affymetrix microarray of such genes. Such gene symbols and aliases are used interchangeably in the present application. In such embodiments, the expression profile of this set of genes may allow the clinician to determine the prognosis of the patient as well as the likelihood that an individual patient to whom the clinical test is administered will respond to a specific form of therapy, such as, for example, chemotherapy. For example, in certain embodiments, a patient having breast cancer may exhibit increased expression of ODC1 (ornithine decarboxylase 1) and EIF4A (eukaryotic translation initiation factor 4A), and decreased expression of RRM2 (ribonucleotide reductase M2 polypeptide), as shown in FIG. 4, and as shown in FIG. 5, a patient having breast cancer who may be more likely to respond to chemotherapy may exhibit an expression profile in which expression of ASPM (abnormal spindle-like microcephaly associated) and RRM2 (ribonucleotide reductase M2 polypeptide) are different than a patient who will most likely not respond, or not respond as definitively, to chemotherapy, compare FIG. 4 and FIG. 5. Notably, the response pattern may be different for different chemotherapy regimens. For example, in FIG. 4 (dataset showing response to Taxol) non-cell cycle genes do not appear elevated in responders and were not predictive. In contrast, in FIG. 5 (dataset showing response to a combination therapy) the cell cycle genes were elevated in responders and could be used to predict a response to combination therapy. These distinctions, which distinguish a patient who will respond to chemotherapy from those who will not, may be observed regardless of the prognosis of the patient, and may be particularly useful in identifying patients with a poor prognosis, late stage, or aggressive form of breast cancer who will respond to chemotherapy from those who will not.

TABLE 1

| | Gene Symbol | Alias(es) | Description | Affymetrix microarray ID |
|---|---|---|---|---|
| 1 | ASPM | FLJ10517 | asp (abnormal spindle) homolog, microcephaly associated (*Drosophila*) | 219918_s_at |
| 2 | NCAPG | HCAP-G; CAPG | non-SMC condensin I complex, subunit G | 218663_at |
| 3 | CDKN3 | CIP2 | cyclin-dependent kinase inhibitor 3 | 209714_s_at |
| 4 | AURKA | STK6; STK15 | aurora kinase A | 204092_s_at |
| 5 | FOXM1 | FKHL16 | forkhead box M1 | 202580_x_at |
| 6 | CEP55 | C10orf3; FLJ10540 | centrosomal protein 55 kDa | 218542_at |
| 7 | TNFRSF6B | DCR3; TR6 | tumor necrosis factor receptor superfamily, member 6b, decoy | 206467_x_at |
| 8 | FGFBP1 | HBP17 | fibroblast growth factor binding protein 1 | 205014_at |
| 9 | CAPRIN2 | C1QDC1 | caprin family member 2 | 218456_at |
| 10 | TUBG1 | TUBG | tubulin, gamma 1 | 201714_at |
| 11 | ZWILCH | FLJ10036 | Zwilch, kinetochore associated, homolog (*Drosophila*) | 218349_s_at |
| 12 | RRM2 | RR2M | ribonucleotide reductase M2 | 209773_s_at |
| 13 | ACTB | — | actin, beta | 200801_x_at |
| 14 | ACTN1 | — | actinin, alpha 1 | 208637_x_at |
| 15 | EPHA2 | ECK | EPH receptor A2 | 203499_at |
| 16 | TRIP13 | 16E1BP | thyroid hormone receptor interactor 13 | 204033_at |
| 17 | CKS2 | CKSHS2 | CDC28 protein kinase regulatory subunit 2 | 204170_s_at |
| 18 | VRK1 | PCH1 | vaccinia related kinase 1 | 203856_at |
| 19 | DUSP4 | MKP2 | dual specificity phosphatase 4 | 204014_at |
| 20 | EIF4A1 | DDX2A | eukaryotic translation initiation factor 4A1 | 214805_at |
| 21 | SERPINE2 | Nexin-1 | serpin peptidase inhibitor, clade E (nexin, plasminogen activator inhibitor type 1), member 2 | 212190_at |
| 22 | ODC1 | EC 4.1.1.17 | ornithine decarboxylase 1 | 200790_at |

Identification of patients who will respond to various forms of chemotherapy may be carried out using the clinical tests of embodiments of the invention. For example, in some embodiments, the clinical test may identify patients who will respond to aklylating agents including for example, nitrogen mustards such as mechlorethamine (nitrogen mustard), chlorambucil, cyclophosphamide (Cytoxan®); ifosfamide, and melphalan; nitrosoureas such as streptozocin, carmustine (BCNU), and lomustine; alkyl sulfonates such as busulfan; triazines such as dacarbazine (DTIC) and temozolomide (Temodar®); and ethylenimines, such as, thiotepa and altretamine (hexamethylmelamine); and the like. In other embodiments, a patient's response to antimetabolites including but not limited to 5-fluorouracil (5-FU), capecitabine (Xeloda®), 6-mercaptopurine (6-MP), methotrexate, gemcitabine (Gemzar®), cytarabine (Ara-C®), fludarabine, and pemetrexed (Alimta®) and the like may be tested, and in still other embodiments, efficacy of anthracyclines such as, for example, daunorubicin, doxorubicin (Adriamycin®), epirubicin, and idarubicin and other anti-tumor antibiotics including, for example, actinomycin-D, bleomycin, and mitomycin-C may be tested.

In yet other embodiments, the clinical test may be directed to identifying patients who will respond to topoisomerase I inhibitors such as topotecan and irinotecan (CPT-11) or topoisomerase II inhibitors such as etoposide (VP-16), teniposide, and mitoxantrone, and in further embodiments, the clinical test may be configured to determine the patients response to corticosteroids such as, but not limited to, prednisone, methylprednisolone (Solumedrol®) and dexamethasone (Decadron®). In particular embodiments, the clinical test may be configured to indentify patients who will respond to anti-mitotic agents including, for example, taxanes such as paclitaxel (Taxol®) and docetaxel (Taxotere®); epothilones such as ixabepilone (Ixempra®); vinca alkaloids such as vinblastine (Velban®), vincristine (Oncovin®), and vinorelbine (Navelbine®); and estramustine (Emcyt®). Without wishing to be bound by theory, the clinician may be capable of determining the efficacy of any or all of the chemotherapy agents identified above based on the expression profile derived from a microarray having probes for same marker genes, and in certain embodiments, a clinician may be capable of distinguishing the efficacy of individual forms of chemotherapy identified above based on microarrays having probes for the same marker genes.

Certain embodiments of the invention are also directed to methods for using the clinical tests of the embodiments described above. For example, various embodiments, may include the steps of obtaining tissue samples from a patient, isolating genetic material and/or proteins from the tissue samples, determining the expression levels of one or more marker genes from the isolated genetic material, developing a genetic profile from the expression levels of the one or more marker genes, and providing treatment to patients whose expression profile matches or nearly matches a predetermined expression profile that indicates that a patient will respond to the treatment. Determining the expression levels of one or more marker genes may be carried out by any method. For example, in some embodiments, the expression levels of one or more marker genes may be measured using polymerase chain reaction (PCR), enzyme-linked immunosorbent assay (ELISA), magnetic immunoassay (MIA), flow cytometry, microarrays, or any such methods known in the art. In particular embodiments, one or more microarray may be used to measure the expression level of one or more marker genes, and in embodiments, the method may further include the steps of labeling the isolated genetic material or proteins and applying the labeled isolated genetic material or proteins to a microarray configured to identify patients who will respond to a form of treatment.

In such embodiments, the step of obtaining tissue samples from a patient may be carried out by any method. For example, in some embodiments, the tissue sample may be obtained by excising tissue from the patient during surgery, and in other embodiments, the tissue sample may be obtained by aspirating tissue or cells from a patient prior to surgery such as a tumor. In particular embodiments, the tissue extracted may be tumor tissue excised during a tumorectomy or an invasive biopsy of a tumor, or aspirated from a tumor as a less invasive means to biopsy the tumor. In various embodiments, the tissue sample may be of diseased tissue. In some embodiments, the tissue sample may be from normal healthy tissue, and in certain embodiments, the tissue sample may include one or more tissue samples from diseased or tumor tissue and normal healthy tissue.

Similarly, the step of isolating genetic material and/or protein may be carried out by any method known in the art. For example, numerous methods for extracting proteins from a tissue sample are known in the art, and any such method may be used in embodiments of the invention. Similarly, numerous methods and kits for extracting DNA and/or RNA from a tissue sample are known in the art and may be used to isolate genetic material or any portion thereof from the tissue sample. In certain embodiments, the step of isolating genetic material form the tissue sample may further include the step of amplifying the genetic material. For example, in some embodiments, mRNA may be isolated from the tissue sample using a known method, and the isolated mRNA may be amplified using PCR or RT-PCR to produce cDNA or cRNA. Methods for amplifying mRNA using such methods are well known in the art and any such method may be used in embodiments of the invention.

Having isolated the proteins and/or genetic material from the tissue sample and, in some embodiments, having amplified the isolated genetic material or a portion thereof, the resulting protein or genetic material may be labeled using any method. For example, in some embodiments, genetic material may be labeled using biotin, and in other embodiments, the genetic material may be labeled using radio-labeled nucleotides or fluorescent label such as a fluorescent nanoparticles or quantum dots. Proteins can be labeled using similar techniques. As above, methods for labeling genetic materials and proteins are well known in the art and any such methods may be used in embodiments of the invention.

The step of applying the labeled proteins or genetic material to a microarray may be carried by any method known in the art. In general, such methods may include the steps of preparing a solution containing the labeled protein or genetic material, contacting the microarray with the solution containing the labeled protein or genetic material, and allowing the labeled protein or genetic material to bind or hybridize to probes associated with the microarray. The various steps associated with applying the labeled proteins or genetic materials to a microarray are well known in the art and can be carried out using any such method. Additionally, in some embodiments, the step of allowing the labeled protein or genetic material to bind or hybridize to probes associated with the microarray may include an incubation step wherein the microarray is immersed in the solution for a period of time from, for example, 15 minutes to 3, 4, 5, or 6 to 12 hours to allow adequate hybridization. In certain embodiments, the incubation step may be carried out at room temperature, and in other embodiments, the incubation step may be carried out at a reduced temperature or an increased temperature as compared to room temperature which may facilitate binding or hybridization.

The step of developing the genetic profile from the microarray may include any number of steps necessary for the clinician to observe the label associated with labeled protein or genetic material and quantify the intensity of the signal derived from the labeled protein or genetic material. For example, in embodiments in which biotin is used to label genetic material, the step of developing the genetic profile of the microarray may include the step of washing the microarray with streptavidin, and in some embodiments, additionally washing the microarray with an anti-streptavidin biotinylated antibody to stain the microarray. The hybridized labeled genetic material may then be observed and the intensity of the signal quantified using fluormetric scanning. In other embodiments in which the protein or genetic material is labeled with a radio-nucleotide, observing and quantifying the intensity can be carried out using emulsion films such as X-ray film or any manner of scintillation counter or phosphorimager. Numerous methods for performing such techniques are known in the art and may be useful in embodiments of the invention. In still other embodiments, nanoparticles or quantum dots may be observed and quantified by exciting the quantum dot under light of a specific wavelength and viewing the microarray using, for example, a CCD camera. The intensity of signal derived from images of the microarrays can then be determined using a computer and imaging software. Such methods are well known and can be carried out using numerous techniques.

In some embodiments, developing the genetic profile may further include comparing the intensities of the signal from one or more probes for genetic markers on the microarray with microarrays derived from normal healthy tissue, of either the same origin or another origin, which may or may not be from the same patient or standard intensities which reflect compiled genetic profiles data from similar clinical tests for numerous individuals having the subject disease such as cancer or breast cancer. In such embodiments, modulated expression of a particular gene may be evident by an increase or a decrease in signal from a probe associated with the particular gene, and an increase or a decrease in a specific gene may by indicative of a genetic profile for a patient who will respond well to a specific form of treatment. For example, a patient whose expression profile exhibits an increase in expression in the RRM2 (ribonucleotide reductase M2 polypeptide) gene over the median intensity for that gene of all patients having breast cancer whose expression profile was determined using the same clinical test or microarray may have a greater likelihood of responding to treatment using chemotherapy, such as, taxane therapy. In some embodiments, the change in intensity may be significant and obvious, for example, a dramatic change (10-fold) in intensity for one or more genetic marker may be observed based on the average expression profile. In other embodiments, a change in intensity may be reflected in about 10% to about 20% reduction in intensity for one or more genetic markers. Without wishing to be bound by theory, detecting this change in intensity and correlating it with a therapeutic sensitivity of an individual may provide a sensitive, fast, and reproducible means for identifying therapeutic agents that will effectively treat the disease and/or tailoring specific therapeutic regimens for individual patients that increase their chances of alleviating or curing the diseased state. For example, in some embodiments, markers in clinical tests for breast cancer may accurately identify individuals that will respond to taxane treatment over breast cancer patients who will not respond to such treatment by detecting a difference in intensity for one or more genetic markers with a p-value from about 0.001 to about 0.00001, and in other embodiments about 0.0001.

Having developed the expression profile of a patient based on the microarray of the clinical test and having determined the therapeutic sensitivity of the patient, the patient may be treated using the appropriate therapeutic agent such as one or more of the chemotherapy agents described above. In some embodiments, the therapeutic agent identified may be administered alone. In other embodiments, the therapeutic agent identified may be administered as part of a course of treatment that may include one or more other forms of treatment. For example, in some embodiments, a therapeutic agent identified using the methods of embodiments of the invention may be provided as a form of neoadjuvant therapy for cancer. In such embodiments, the identified therapeutic agent may be administered to the patient before radiation or surgery to reduce the size of a tumor, and reducing the size of the tumor may reduce the amount of tissue removed during surgery. For example, in breast cancer, neoadjuvant therapy has been shown to increase the likelihood of a successful lumpectomy, which conserves breast tissue while removing the tumor reducing the need for a mastectomy in which one or both breasts are completely removed. Thus, embodiments of the method may include the steps of administering a therapeutic agent identified using the clinical test alone or in combination with one or more other forms of therapy, and/or the step of administering the therapeutic agent identified as a form of neoadjuvant therapy for cancer, and in particular embodiments, breast cancer.

Still other embodiments of the invention may include kits for determining an appropriate therapeutic agent to treat a disease that includes the clinical test of embodiments described above, and one or more additional elements for preparing an expression profile from a tissue sample using the clinical test. For example, in some embodiments, a kit may include an apparatus for collecting a tissue sample, a means for determining the expression levels of one or more genes associated with the disease, labels, reagents, and other materials necessary to determine the expression profile, and instructions for identifying a therapeutic agent based on the expression profile. Determining the expression levels of one or more marker genes may be carried out by any method such as polymerase chain reaction (PCR), enzyme-linked immunosorbent assay (ELISA), magnetic immunoassay (MIA), microarrays, or any such methods known in the art, and the contents of the kits of various embodiments may vary based on the method utilized. For example, in some embodiments PCR may be the method for determining the expression level of one or more marker genes, and the kit may include single-stranded DNA primers which facilitate amplification of a marker gene. In other embodiments, ELISA or MIA based kits may include antibodies directed to a specific protein and/or fluorescent or magnetic probes. In particular embodiments, one or more microarray may be used to measure the expression level of one or more marker genes, and such kits may include one or more microarrays having probes to specific marker genes.

In a preferred embodiment, the disease may be cancer or pre-cancer. In yet another preferred embodiment, the cancer may be breast cancer.

Any apparatus for collecting a tissue sample may be used in the various embodiments of the invention. For example, in some embodiments, the apparatus may be a needle and/or syringe used to aspirate cells or tissue from diseased tissue such as a tumor. In other embodiments, the kit may include a scalpel or other instrument for obtaining a tissue sample. In still other embodiments, the kit may include a combination of apparatuses that may be used to obtain a tissue sample. In further embodiments, the kit may include an instruction describing the use of another commercially available apparatus to obtain a tissue sample.

In some embodiments, one or more labels for the protein or genetic material may also be provided in the kit. For example, kits of various embodiments may include a label, such as biotin and the reagents and materials necessary to perform biotinylation, a radio-label or radio-labeled nucleotide and reagents and materials necessary to incorporate a radioactive label into isolated protein or genetic materials, fluorescent label and reagents and materials necessary to fluorescently label the isolated protein or genetic material, nanoparticles, nanocrystals, or quantum dots and reagents and materials necessary to label the isolated protein or genetic material with nanoparticles, nanocrystals, or quantum dots, and combinations thereof.

Numerous reagents may be provided in the kits of embodiments of the invention including, for example, reagents necessary for tissue sample acquisition and storage, reagents necessary for protein and/or genetic material isolation, reagents necessary for labeling, reagents necessary to perform PCR, ELISA, MIA, or using a microarray, reagents for producing a solution used to apply labeled protein or genetic material to the microarray, reagents necessary for developing the microarray, reagents used in conjunction with observing, analyzing or quantifying the expression levels, the expression profile, reagents for the storage of the microarray following processing, and the like and combinations thereof. In some embodiments, the kit may include vials of such reagents in solution arranged and labeled to allow ease of use.

In other embodiments, the kit may include the component parts of the various reagents which may be combined with a solvent such as, for example, water to create the reagent. The component parts of such embodiments may be in solid or liquid form where such liquids are concentrated to reduce the size and/or weight of the kit thereby improving portability. In still other embodiments, the various reagents necessary to use the clinical test of various embodiments may be supplied by providing the recipe and or instructions for making the reagents or exemplary reagents that may be substituted by other commonly used similar reagents.

In certain embodiments, the kits of the invention may include materials necessary to develop a microarray. For example, in some embodiments, the kit may include an apparatus for holding the microarray and/or sealing at least an area surrounding the microarray to ensure that solutions containing labeled proteins or genetic material remain in contact with the microarray for a sufficient period of time to allow adequate binding or hybridization. In other embodiments, the kit may include apparatuses for ease of handling the microarray during development. In still other embodiments, the kits of the invention may include a means for observing the labeled protein or genetic material on the microarray and/or quantifying the intensity of the signal generated by the labeled protein or genetic material. In still other embodiments, the kit may include exemplary data, charts, and intensity comparison markers. In some such embodiments, these or other similar materials may be provided in written form, and in other such embodiments, these or other similar materials may be provided on a computer readable medium, such as a CD, DVD, Blue-Ray or any other data storage device. In yet other such embodiments, various materials may be provided through an internet website accessible to kit purchasers. Similarly, instructions for using the kit and any materials supplied with the kit may be provided with purchase of the kit in written form, on a computer readable medium, or on a similar internet website.

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

EXAMPLES

Example 1

The expression profiles of 22,283 transcripts using Affymetrix HG-U133A microarrays were analyzed to systematically probe the molecular changes that accompany acinus formation. Microarray experiments were performed with biological duplicates using RNA samples harvested from S1 and 184 cells, after 3, 5, and 7 days' culture in three-dimensional (3D) laminin-rich extracellular matrix (lrECM). lrECM cultures permit non-malignant cells to exhibit self-organizing properties. Such cultures provide models that allow the study of processes that are aberrant in breast cancer and how breast epithelial cells transition from a proliferating, unorganized state to a resting, organized state, and to relate this process to the opposing changes that occur in clinical breast cancer. Genome-wide gene expression profiling for two independently derived non-malignant human mammary epithelial cells (HMEC), one finite lifespan strain (184) and one spontaneously immortalized line (HMT3522 S1). Both cells formed acinus-like structures with similar morphology and basal polarity when cultured from single cells in lrECM in 3D cultures.

Comparison of the decrease in the percentages of cells in S-phase showed that growth arrest occurred with kinetics that were significantly correlated (>95% confidence level) in both cell types (correlation coefficient=0.89). Further, the S-phase decrease was significant (p=0.05, ANOVA). Hence, the gene expression changes important for these processes were assumed to follow a common temporal pattern in both cell lines, and that changes that were cell type-specific could be disregarded.

Cell samples were harvested in duplicate at three time points, 3, 5, and 7 days, after seeding in lrECM. Purified total cellular RNA was biotin-labeled and hybridized to human oligonucleotide microarrays (Affymetrix HG-U133A). Experiments with Affymetrix-present P-call rates of >30% were included in the analysis. Signal values from each of the 22,283 probe sets were calculated by means of robust multi-array analysis (RMA) using Bioconductor in the R computing environment. The signal values were inverse log 2 transformed and then imported into GeneSpring software (SiliconGenetics, Palo Alto, Calif.), and each array was normalized to its median signal intensity. The genes were normalized to the mean of the 3-day time point for each cell type independently.

Method 1: Significantly up-regulated genes in each cell specimen were identified by first selecting the genes induced at least 1.5 fold in at least one of the six conditions and then performing an ANOVA analysis as a function of time. Variances were calculated using the cross-gene error model (GeneSpring), p-value cutoff of 0.05 and multiple testing correction of Benjamini and Hochberg False Discovery Rate. About 5% of the identified genes in each set would be expected to pass this restriction by chance. Significantly down-regulated genes were identified in the same manner after normalizing to the 7-day time point. Genes that were up- or down-regulated early in each cell line were selected from the significantly up- or down-regulated gene lists. The early genes were defined as those with a mean expression at 5 days of at least 50% of their mean expression at 7 days.

Method 2: All genes that were at least 1.5 fold differential (up or down) in at least one of the four samples from the two later time points (days 5 and 7) for either cell specimen were selected. ANOVA was then performed as a function of time. Variances were not assumed equal (Welch ANOVA), p-value cutoff of 0.05 and multiple testing correction of Benjamini and Hochberg False Discovery Rate. From this list of genes that were significantly differential in either cell line, genes that were up- or down-regulated early (mean expression at 5 days of at least 50% of their mean expression at 7 days) or late in each cell line were then identified. Accordingly, those genes that were coordinately regulated in both cell lines were identified.

Genes were identified that showed at least 1.5-fold change during the time course in the individual cell specimens (ANOVA, p<0.05), and 363 genes were found to be up-regulated and 117 genes down-regulated in 184 cells; 234 genes were up-regulated and 351 genes down-regulated in S1 cells. These lists were then divided into 'early' genes whose expression was modulated between days 3 and 5 or 'late' genes whose expression was modulated between days 5 and 7 in S1 and 184. A total of 60 genes with common temporal patterns were identified, including 21 genes that were up-regulated early, 11 genes that were up-regulated late, 6 genes that were down-regulated early and 22 genes that were down-regulated late. The magnitude of the expression changes of the 22 down-regulated genes in HMEC ranged from 2.5-fold (ACTB) to 5.4-fold (TRIP13).

To relate the process of acinar development in 3D lrECM cell cultures to the changes that occur in breast cancer, the expression levels of the differentially regulated genes identified were examined using previously published microarray data for a panel of 295 breast cancer samples from the fresh-frozen-tissue bank of the Netherlands Cancer Institute, including 151 lymph node-negative disease and 144 lymph node-positive disease patient samples (van de Vijver, et al., N. Engl. J. Med., 347:1999-2009 (2002)). Fifty five of the 60 genes selected in our 3D culture analysis were included on these microarrays.

Student's t-test was next applied to the 5- and 10-year survival data to determine how many of the genes modulated in 3D cultures showed survival-associated expression changes. T-tests were performed to determine whether the difference in the expression level of a given gene in two groups (e.g., patients who survived five years versus patients who did not) was large enough that it was not likely to be due to chance. The numbers and percentages of genes exhibiting significantly different expression in the tumors of patients with differential survival (p<0.05) were tabulated for a) all the genes represented on the microarrays; b) genes selected on the basis of differential expression during the 3D lrECM time course; or c) randomly generated gene lists. The percentage of genes with survival-associated expression changes was highest for those genes down-regulated late, between days 5 and 7, in the time course. The percentage for this gene list exceeded those of the unfiltered list of all 25,773 genes represented on the arrays, 5 random gene lists, and all other 3D lrECM gene lists. The list of genes that were down-modulated late in the lrECM timecourse showed a marked enrichment in genes the expression level of which correlated to 5 (68%) and 10 years survival (53%). The levels of the majority of the late down-regulated genes were higher in patients who died within 5 or 10 years (ACTB, VRK1, ODC1, CKS2, FLJ10036, FLJ10540, FOXM1, RRM2, TRIP13, CDKN3, STK6, FLJ10517, TUBG1, ACTN1, TNFRSF6B and EPHA2), while the levels of three genes (DUSP4, HBP 17 and EIF4A1) were lower in these patients. The magnitude of the expression changes of the down-regulated genes in the 250 tumor samples ranged from 1.5-fold (FLJ10036) to 9.3-fold (HPV 17).

As shown in FIG. 1, twenty-two (22) genes were found to be down-regulated in both HMECs between days 5 and 7 of lrECM culture. Of these, 19 genes were represented in the published data set for the 295 patient tumor samples. The 295 breast cancer samples from the fresh-frozen-tissue bank of the Netherlands Cancer Institute were stratified into quartiles based on the relative expression level of each of the genes in the selected set, and further analyzed the relationship of the expression level of each individual gene to survival. The resulting Kaplan-Meier curves showed that gene expression levels correlated significantly with outcome for 14 of the 19 selected markers. For 13 of the 14 markers, gene expression was lower in tumors from patients with better outcomes, while in one case (DUSP4) gene expression was lower in tumors from patients with poorer outcomes.

To test whether expression levels of the 19 selected marker genes correlated with lymph node status, a Pearson product-moment correlation coefficients was calculated. Although no genes were correlated at the 95% confidence level, expression levels of 4 of the 19 genes showed a trend toward a correlation with lymph node number or status (80% confidence level) including DUSP4, HBP 17, TNFRSF6B and TUBG1.

Next, the ability to classify breast cancer patients into prognostic groups was tested. Hierarchical cluster analysis was used to separate the patients into groups and then determined the overall 10-year survival rates for these groups. The cluster analysis separated the patients into five groups, three of which had tumors that expressed comparatively lower levels of most of the 19 genes, and two of which expressed higher levels. The 10-year survival rates for these 5 groups were 95%, 84%, 67%, 61%, and 54% respectively.

To test whether other sets of genes down-regulated late in the lrECM timecourse identified using other selection strategies would also include useful breast cancer markers, a second selection strategy was applied and the ability of the resulting gene set to predict breast cancer prognosis was tested. This second method was less restrictive than the first, and resulted in the identification of 287 genes that were significantly down-regulated late in the 3D time course of both HMEC specimens. Seventeen of the 22 genes selected using Method 1 were also included in the 287 genes selected using Method 2.

Hierarchical cluster analysis using the 249 gene signature classified the samples into two groups of approximately equal numbers of tumors. Overall 10 year survival rates were 90% (138 of 154) for the good prognosis group and 59% (83 of 141) for the poor prognosis group. To assess the significance of these predictions and take into account patients that could not be followed the entire length of the study, a Kaplan Meier analysis was performed. The results show that the 249 gene profile was highly informative in identifying patients with poor outcome (log rank $p=2.7\times10^{-10}$). The estimated hazard ratio for poor outcome (i.e., failure to survive) in the group with the poor prognosis signature as compared with the good prognosis signature was 4.7 (95% confidence interval 2.8-7.9). The 249-gene signature predicted 10-year survival rates of 59% and 90% for poor and good prognosis groups, respectively. The estimated hazard ratio for poor outcome (failure to survive) in the group with the poor prognosis signature as compared with the good prognosis signature was 4.7 (95% confidence interval 2.8-7.9)

The 19-gene signature included several genes encoding proteins with roles in the cell cycle and in cell division that are important markers of prognosis in ER-positive younger patients. Similarly, a core group of predominantly cell cycle and mitotic organizing center genes (CDKN3, RRM3, FLJ10540, FOXM1, STK6, TRIP13, EIF4A1, FLJ10036, VRK1, TUBG1, CKS2, FLJ10517) made a strong contribution to stratifying tumors into good versus poor prognostic groups.

In addition to cell-cycle genes, the prognostic genes also encoded products with functions, including cytoskeletal regulation (ACTB, ACTN1), cell survival (TNFRSF6B), a newly identified member of tumor necrosis factor receptor superfamily (TR6) suppresses LIGHT-mediated apoptosis, and cell-cell interactions (EPHA2). The genes in these groups are important in subdividing the patients into subgroups with differing survival rates.

In conclusion, the gene expression changes that commonly occur in non-malignant HMEC grown in 3D lrECM cultures provide gene expression signatures that effectively stratify patients into prognostic groups according to overall survival rates. The 249 gene signature achieved a hazard ratio of 4.7, which is comparable to hazard ratios achieved by large scale supervised breast cancer microarray studies. These results underscore the relevance of 3D lrECM cultures for studies of malignant transformation, and suggest potentially valuable new biomarkers for further clinical evaluation.

Example 2

The 22 gene signature includes cell cycle and transcription related genes that predict prognosis in ER+ breast cancer patients. This finding shows that proliferation and cell cycle genes are the strongest predictor for relapse among ER positive patients. The use of gene-expression profiling to better understand the clinical heterogeneity of estrogen receptor positive breast cancers and tamoxifen response. In several previous studies, a signature enriched in cell cycle related genes has been reported to predict poor prognosis of breast cancer, along with a second smaller class of genes that includes transcription related genes. Poor prognosis in ER+ tumors in particular has been found to be strongly predicted by over expression of cell cycle and cell proliferation genes.

The 22 gene signature also includes angiogenesis and motility genes that are markers for prognosis in both ER+ and ER− tumors. Genes in this functional class of breast tumor marker genes were also identified in other breast cancer signatures, though the association of this functional class with ER− tumors has not been noted for gene signatures. Markers for ER− tumors have been reported to be significantly less prevalent than markers for ER+ tumors. Some genes within this functional class predicted prognosis for only ER+ tumors, some predicted prognosis for only ER− tumors, and some predicted prognosis for both ER+ and ER− tumors.

Since few overlaps have been found among the published breast cancer signatures, it appears that many (thousands) of marker genes have predictive ability in different subsets of patients. It has been proposed that some genes may have moderate predictive ability in many patients, while some may be "master genes" with high predictive ability in as yet undefined subsets of patients. When many such genes are used together, a highly accurate predictive tool results that is accurate across a wide cross section of breast cancer patients. The actual composition of the signature may be less important than the fact the each signature is a set of many semi-predictive genes. In contrast to gene signatures identified from specific patient sets by supervised methods, the current approach is based on a biologically relevant model system that mimics the human mammary gland. Hence, the 3D-signature holds promise to include "master genes" of key biological processes of cancer. Several examples come from existing literature.

Several of the genes identified are up-regulated in tumor cell lines, implicated in tumor growth, angiogenesis and/or metastasis in animal models, and are under investigation for development of novel target therapies. The EphA2 receptor tyrosine kinase is frequently overexpressed in aggressive breast cancer and has been associated with breast tumor growth in animal models and resistance to therapy with tamoxifen. Reduction in EphA2 expression is currently being considered as a potential target for therapy using monoclonal antibodies to down modulate EphA2 and siRNA studies to inhibit the growth of human breast and lung tumor xenografts in nude mice and tumor angiogenesis and metastatic progression.

Among the most predictive subset of genes are aurora kinase A (AURKA) and CEP55. AURKA is a validated therapeutic target for treatment of cancers and there currently are small molecule inhibitors of aurora kinases being evaluated in the clinic. CEP55 has been identified as a regulator required for cell cycle progression and completion of cytokinesis by loss-of-function studies and it is overexpressed in several cancer cell lines.

The transcription factor forkhead box M1 (FOXM1) has been shown to be up-regulated in a variety of carcinoma cell lines and its expression is suppressed in terminally differentiated cells. Its up-regulation has been shown to lead to proliferation of tumor cells and the formation of lung tumors in transgenic mice while its down regulation has been shown to lead to the inhibition of invasion and angiogenesis in pancreatic cancer cells. For these reasons, inhibitors of FOXM1 are currently under investigation to develop anticancer drugs.

The lesser known gene TRIP 13, a thyroid hormone receptor interactor, is a protein that interacts with hormone-dependent transcription factors to regulate the expression of a variety of specific genes, suggesting that it could have a relevant role in breast cancer biology and be a target for development of novel therapeutics. To determine whether changes in gene expression that occur during acini formation of non-malignant HMEC in a 3D culture model are opposite from those occurring during the development of breast tumors with a poor prognosis, data was generated that show that genes that were expressed at significantly lower levels in organized, growth arrested HMEC than in their proliferating counterparts could be used to classify breast cancer patients into poor and good prognosis groups. The prognostic value of the 22 gene signature identified in Example 1 was confirmed in three independent studies using an unsupervised strategy.

Figure 2:
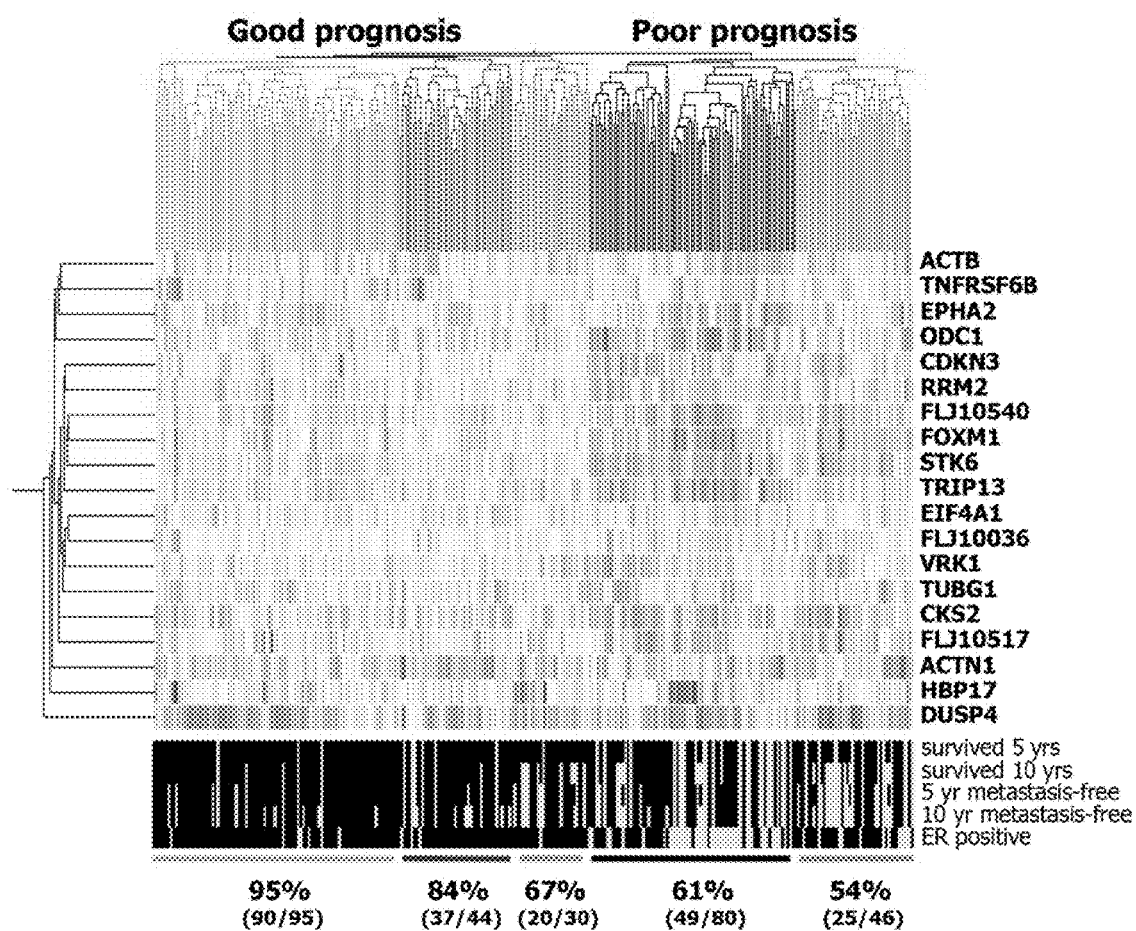
FIG. 2 shows the expression profiles and Kaplan-Meier analysis for breast cancer patients.
Figure 3:
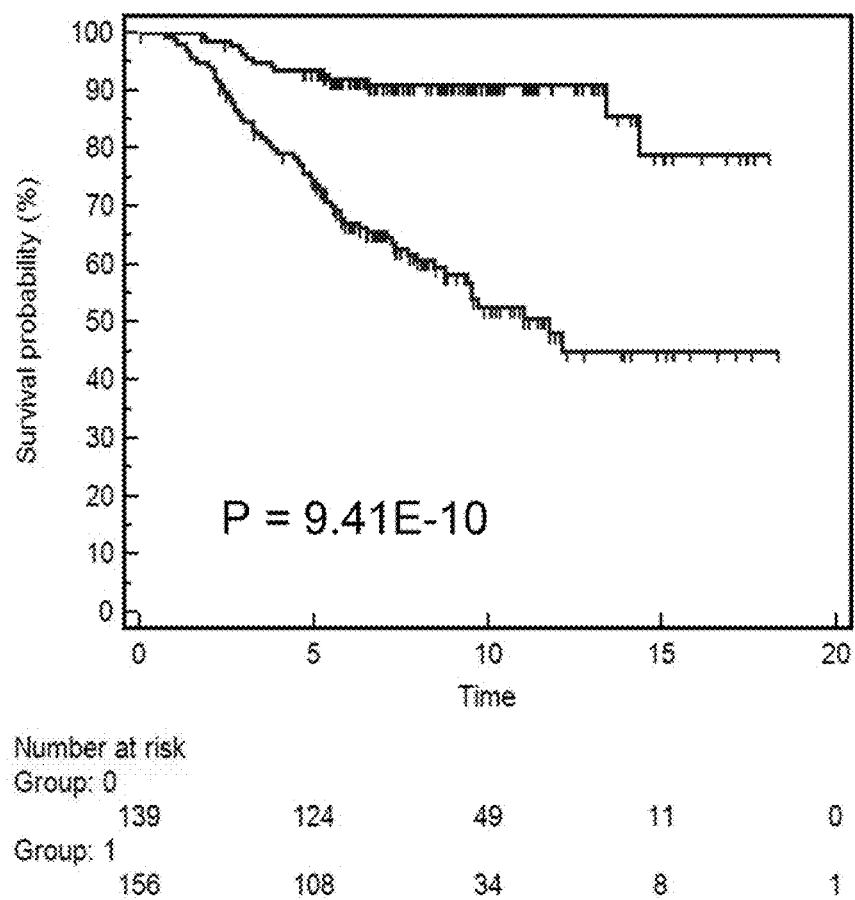
FIG. 3 shows the probability of survival over time for the breast cancer patients.

To test whether the 22 gene signature identified in 3D cultures could predict the prognosis of breast cancer, an unsupervised strategy was used against three large independent datasets representing a total of 699 breast cancer patients and analyzed using Kaplan-Meier analysis: from Wang, et al., p=1.3E-5, Sorlie, et al., p=0.045, and van de Vijver, et al, p=9.4E-10. The results are illustrated in FIG. 2, and the probability of survival over time is provided in FIG. 3. These data suggest that breast tumors with profiles most like differentiating acini (blue clusters) had the best outcome. The multivariable proportional-hazards analysis of 10 year survival risk provided in Table 2 indicate that the 22-genes signature may provide a strong independent factor to predict breast cancer outcome. Results were calculated using the dataset of van de Vijver, et al. using overall survival as the endpoint. Similar results were obtained for the same multivariable analysis using relapse as the endpoint, 3D signature Hazard ratio 3.3 (95% CI 2.0 to 5.3), p<0.0001.

TABLE 2

|  | Hazard ratio (95% CI) | p |
| --- | --- | --- |
| Age (per 10 year increment) | 0.62 (0.44 to 0.88) | 0.008 |
| Tumor diameter (per cm) | 1.33 (1.04 to 1.69) | 0.023 |
| ER (positive vs negative) | 0.55 (0.34 to 0.90) | 0.018 |
| Lymph node status (per positive node) | 1.07 (0.96 to 1.20) | 0.234 |
| Chemotherapy | 0.69 (0.38 to 1.26) | 0.234 |
| Mastectomy | 1.05 (0.63 to 1.73) | 0.864 |
| 3D signature | 4.43 (2.32 to 8.46) | 0.00001 |

Example 3

To determine whether the 22-gene signature can be used to predict a patient's response to treatment, two published breast cancer datasets were used to identify patients that are more likely to respond to neoadjuvant Docetaxel or paclitaxol/FAC treatment.

In the Chang, et al. dataset, the overview of which is provided in Table 3, core biopsies from 24 patients with locally advanced breast cancer were obtained before neoadjuvant docetaxel treatment which included 3-weekly administrations of Tx4 100 mg/m$^2$ docetaxel, and the subjects' response this to treatment was assessed after chemotherapy.

TABLE 3

Table 1. Patient and Tumor Characteristics of Patients Enrolled Onto Phase II Study of Neoadjuvant Docetaxel

| Patient No. | Age (years) | Menopausal Status | Ethnicity | Presenting Tumor Size (cm) | Clinical Axillary Nodes | Histologic Type | ER | PR | HER-2* |
| --- | --- | --- | --- | --- | --- | --- | --- | --- | --- |
| 1 | 37 | Pre | Hispanic | 10 × 10 | No | IMC | Negative | Negative | Negative |
| 2 | 55 | Post | Hispanic | 10 × 8 | Yes | IDC | Negative | Negative | Positive |
| 3 | 41 | Pre | Black | 6 × 5 | Yes | IDC | Positive | Positive | Negative |
| 4 | 43 | Pre | Black | 15 × 13 | Yes | IMC | Positive | Negative | Negative |
| 5 | 50 | Post | Black | 20 × 23 | Yes | IDC | Negative | Negative | Negative |

TABLE 3-continued

Table 1. Patient and Tumor Characteristics of Patients Enrolled Onto Phase II Study of Neoadjuvant Docetaxel

| Patient No. | Age (years) | Menopausal Status | Ethnicity | Presenting Tumor Size (cm) | Clinical Axillary Nodes | Histologic Type | ER | PR | HER-2* |
|---|---|---|---|---|---|---|---|---|---|
| 6 | 55 | Post | Black | 11 × 11 | Yes | IDC | Positive | Positive | Negative |
| 7 | 42 | Pre | Black | 7 × 9 | Yes | IMC | Positive | Positive | Negative |
| 8 | 63 | Post | Black | 7 × 8 | Yes | IMC | Positive | Positive | Negative |
| 9 | 50 | Post | Black | 13 × 9 | No | IDC | Positive | Positive | Negative |
| 10 | 38 | Pre | Hispanic | 8 × 8 | Yes | IMC | Positive | Positive | Negative |
| 11 | 58 | Post | Hispanic | 7 × 7 | Yes | IMC | Positive | Positive | Negative |
| 12 | 62 | Post | Hispanic | 4 × 4 | Yes | IDC | Positive | Negative | Negative |
| 13 | 40 | Pre | Hispanic | 5.5 × 4.5 | No | IMC | Positive | Positive | Negative |
| 14 | 36 | Pre | Black | 6 × 6 | Yes | IDC | Positive | Positive | Negative |
| 15 | 56 | Post | Black | 5 × 5.5 | No | IMC | Positive | Negative | Negative |
| 16 | 38 | Pre | White | 6 × 6 | Yes | IDC | Positive | Negative | Negative |
| 17 | 54 | Post | White | 5 × 6 | Yes | IDC | Positive | Positive | Positive |
| 18 | 52 | Post | White | 10 × 10 | No | IDC | Positive | Positive | Negative |
| 19 | 57 | Post | White | 8 × 8 | No | IDC | Negative | Negative | Negative |
| 20 | 52 | Post | Black | 10 × 10 | No | IDC | Negative | Negative | Negative |
| 21 | 44 | Pre | Black | 11 × 11 | No | IDC | Negative | Negative | Negative |
| 22 | 41 | Pre | Black | 6 × 5 | Yes | IDC | Positive | Positive | Negative |
| 23 | 38 | Pre | White | 8 × 8 | Yes | IDC | Positive | Positive | Negative |
| 24 | 54 | Post | Black | 9 × 7 | No | IDC | Positive | Positive | Negative |

Abbreviations: Pre, premenopausal; Post, postmenopausal; ER, estrogen receptor; PR, progesterone receptor; HER-2, human epidermal growth factor receptor 2; IMC, invasive mammary carcinoma; IDC, invasive ductal carcinoma.
*HER-2/neu oncogene by immunohistochemistry.

In the Hess, et al. dataset, Table 4, Fine-needle aspirates from 133 patients with stage I-III breast cancer were obtained before neoadjuvant treatment, and their response was assessed after chemotherapy.

TABLE 4

| | All tumors | |
|---|---|---|
| | No. | % |
| Female | 133 | 100 |
| Age, years | | |
| Median | na | na |
| Range | 28-79 | |
| Histology | | |
| Invasive ductal | 123 | 92 |
| Mixed duct/lob | 6 | 5 |
| Invasive lobular | 1 | 1 |
| Inv mucinous | 2 | 2 |
| TNM stage | | |
| T1 | 13 | 10 |
| T2 | 70 | 53 |
| T3 | 22 | 17 |
| T4 | 28 | 21 |
| N0 | 40 | 30 |
| N1 | 63 | 47 |
| N2 | 14 | 11 |
| N3 | 16 | 12 |
| Nuclear grade(MBMN) | | |
| 1 | 2 | 2 |
| 2 | 47 | 35 |
| 3 | 62 | 47 |
| ER positive | 81 | 61 |
| ER negative | 63 | 47 |
| HER-2 positive | 33 | 25 |
| Her-2 negative | 99 | 74 |
| Neoadjuvant therapy | | |
| weeklyT × 12 + FAC × 4 | 115 | 86 |
| 3-weeklyT × 4 + FAC × 4 | 18 | 14 |

TABLE 4-continued

| | All tumors | |
|---|---|---|
| | No. | % |
| Pathologic complete response | 34 | 26 |
| Residual disease | 99 | 74 |

Abbreviations: MBMN. modified Blacks nuclear grade. T. paclitaxel: FAC flurocil, doxorubicin, and cyclophosphamide. ER positivity determinied by immunohistochemistry.

Cluster analysis was used to group the 24 tumors into 2 groups based on expression patterns of the 22-genes signature for the Chang, et al. dataset as shown in FIG. 4. Significantly more taxol resistant tumors were included in the left (blue) cluster (13 of 14); while significantly more taxol sensitive tumors were included in the right (red) cluster (9 of 10). This analysis includes the 17 out of 22 genes on the HG-U95AV2 chips. Duplicate probesets were included for 3 genes (20 total probesets). If single probesets are used instead of the duplicates, the signature still accurately predicts response (p=0.0022, Fisher's Exact test). The HG-U95V2 microarray used to assess the expression profile of the Chang, et al. dataset does not include ASPM, NCAPG, CEP55, CAPRIN2, or ZWILCH which are part of the 22-gene signature. Thus, these genes are absent in the data provided in FIG. 4.

Cluster analysis was used to group the 133 tumors of the Hess dataset into 2 groups based on expression patterns of the 22-genes as shown in FIG. 5. Significantly more taxol resistant (RD) tumors were included in the right cluster (60 of 66); while significantly more taxol sensitive tumors (pCR) were included in the left cluster (28 of 67). Notably, this analysis includes all 22-genes of the 22-gene signature.

To further verify these results, ROC analysis was carried out for both the Chang, et al. dataset and the Hess, et al. data set. Briefly, ROC graphs are two dimensional graphs in which the true positive rate (tp) is plotted on the Y axis and false positive rate (fp) is plotted on the X axis, as shown in FIG. 6. An ROC graph depicts tradeoffs between benefits (true positives) and costs (false positives, 1.00=no false negatives). Area under the curve (AUC) is a summary statistic that combines the sensitivity (1.00=no false positives) and specificity (1.00=no false negatives) into a single measure. An AUC of 1.0 is considered a perfect test (A+), and lower AUC measures indicate poorer data as follows: 0.9-0.999 excellent (A); 0.8-0.899 good (B); 0.7-0.799 fair (C), 0.6-0.699 poor (D), and 0.5-0.599 failure (F).

Table 5 shows ROC analysis summary statistics for the 24 tumors of the Chang, et al. dataset. The overall taxol sensitive rate for the 24 tumors was 41.7% (10 of 24). The 22-genes signature was the most accurate to predict sensitive tumors (sensitivity 0.9) with p-value of 0.0001. AUC value for the 22-genes suggests a good test.

TABLE 5

|  | 22-gene signature | MammaPrint (70 genes) | Hess (30 genes) | ER status | Her2 status | Irrelevant list (9 mast cell specific genes) | Random list (29 genes) |
| --- | --- | --- | --- | --- | --- | --- | --- |
| Positive group (sensitive) | 10 | 10 | 10 | 10 | 10 | 10 | 10 |
| Negative group | 14 | 14 | 14 | 14 | 14 | 14 | 14 |
| Sensitivity (accurate prediction of sensitive tumors) | 0.9 | 0.8 | 0.8 | 0.8 | 0.3 | 0.4 | 0.6 |
| Specificity (accurate prediction of resistant tumors) | 0.78 | 0.85 | 0.5 | 0.35 | 0.78 | 0.71 | 0.5 |
| Area under the curve (AUC) | 0.84 | 0.83 | 0.65 | 0.58 | 0.54 | 0.56 | 0.5 |
| Standard error of AUC | 0.0879 | 0.0913 | 0.113 | 0.119 | 0.122 | 0.122 | 0.121 |
| P-value | 0.0001 | 0.0003 | 0.1860 | 0.5097 | 0.7254 | 0.6389 | 0.6785 |

Table 6 shows the ROC analysis summary statistics for the 133 tumors of the Hess, et al. dataset. The overall pCR rate in the 133 patients was 26% (n=34). 22-genes signature, Hess, 30 genes and tumor grade were the best predictors (sensitivity >0.8) with significant p-values. AUC values for the 22-genes suggest a fair test. The values tabulated here differ from those reported in Hess, et al due to the following differences: 1) Different methods were used to calculate and normalize signal values from the Affymetrix CEL files (Hess: dCHIP reference chip method; here: RMA via GeneSpring). 2) Hess, et al. calculated ROC summary statistics using a subset of only 51 tumor samples (since they used the other 81 as a training set), whereas this tabulation is based on the entire set of 133 tumor samples.

TABLE 6

|  | 22-gene signature | MammaPrint (70 genes) | Hess (30 genes) | ER status | Her2 status | Irrelevant list (9 mast cell specific genes) | Random list (29 genes) |
| --- | --- | --- | --- | --- | --- | --- | --- |
| Positive group (sensitive) | 34 | 34 | 34 | 34 | 33 | 34 | 34 |
| Negative group | 99 | 99 | 99 | 99 | 99 | 99 | 99 |
| Sensitivity (accurate prediction of sensitive tumors) | 0.82 | 0.76 | 0.82 | 0.79 | 0.39 | 0.70 | 0.70 |
| Specificity (accurate prediction of resistant tumors) | 0.62 | 0.70 | 0.70 | 0.76 | 0.80 | 0.33 | 0.49 |

TABLE 6-continued

|  | 22-gene signature | MammaPrint (70 genes) | Hess (30 genes) | ER status | Her2 status | Irrelevant list (9 mast cell specific genes) | Random list (29 genes) |
|---|---|---|---|---|---|---|---|
| Area under the curve (AUC) | 0.72 | 0.73 | 0.76 | 0.78 | 0.6 | 0.52 | 0.60 |
| Standard error of AUC | 0.0543 | 0.0537 | 0.0515 | 0.0415 | 0.0587 | 0.0579 | 0.058 |
| P-value | 0.0001 | 0.0001 | 0.0001 | 0.0001 | 0.1023 | 0.7776 | 0.0834 |

ROC analysis shows that the 22-gene signature is a fair (AUC=0.720) and statistically significant (p=0.0001) overall predictor of drug response. In particular, it is a good predictor of patients who will respond with complete response to therapy (true positives) (sensitivity=82.35).

Patient stratification was performed using expression levels of the 22 genes measured from tumor biopsy samples that were obtained prior to chemotherapy treatment with a taxane-based regimen. Gene expression levels were measured using cDNA microarrays. Expression for each gene was normalized to the mean expression level of that gene for the entire set of samples being analyzed. Hierarchical cluster analysis was used to stratify patients. Hierarchical clustering was performed using GeneSpring software and used a Standard correlation metric with average linkage in the sample dimension. Cut-offs were set at separation ratio of 1 and minimum distance of 0.001.

Hierarchical clustering can be used to predict the outcome of newly added individual patients. New patients with unknown outcome can be mapped onto previously clustered patient profiles. Mapping is performed using a Pearson correlation metric to compare the expression levels of the 22 signature genes of a new patient with all patients of the previously clustered dataset. This method was used to stratify ten additional patients according to prognosis, correlation coefficients ranged from 0.53 to 0.75. Four of the ten patients mapped to the good prognosis cluster and six to the poor prognosis cluster. Only one the four experienced a relapse within 10 years of follow up (relapse times were 10.5, 1.2, 17.8, and 16.5 years). Of the six that mapped to the poor prognosis cluster, five relapsed within 10 years (relapse times were 6.0, 15.9, 2.0, 0.5, 1.4, and 1.9 years).

Embodiments of the present invention are directed to methods for predicting the efficacy of treatment of breast cancer comprising analyzing an expression profile of marker genes from a cancerous breast tissue and predicting the efficacy of treatment if the expression profile from the cancerous breast tissue matches a predetermined expression profile that indicates a patient will respond to the treatment. In certain embodiments, the marker gene is selected from a group consisting of ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof. In another embodiment, the method may further comprise developing an expression profile from the marker genes. In yet another embodiment, a method may further comprise generating a report indicating the likelihood of long-term survival with breast cancer recurrence in the patient.

In another embodiment, methods for predicting the efficacy of treatment of breast cancer comprise a chemotherapeutic agent, radiation and a combination thereof. In another embodiment, the chemotherapeutic agent comprises alkylating agents, antimetabolites, anthracyclines, anti-tumor inhibitors, topoisomerase I inhibitors, topoisomerase II inhibitors, corticosteroids and combinations thereof. In a preferred embodiment, the therapeutic agent is an anti-mitotic agent. In yet another embodiment, the anti-mitotic agent is a taxane.

In yet another embodiment, chemotherapy is provided to the patients after gene expression profiling.

In yet another embodiment, a kit for testing therapeutic sensitivity of breast cancer tissue is disclosed. The kit may comprise a means for identifying the expression profile of a tissue sample having probes to a specific set of genes or proteins associated with the disease; and labels, reagents, and other materials or instructions for labeling and preparing reagents and other materials necessary to develop an expression profile of one or more marker genes. In another embodiment, the marker genes comprise ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof.

In another embodiment, a clinical test for breast cancer comprising a means of detecting an expression pattern of one or more marker genes from diseased tissue of a patient is described, wherein the expression level of at least one of the one or more genes is modulated compared to normal tissue and other diseased tissue; and wherein the modulation of the at least one gene is indicative a diseased tissue that is sensitive to a specific therapeutic agent. In another embodiment, the marker genes may comprise ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof.

In yet another embodiment, a method of identifying a breast cancer patient who is likely to respond to a treatment for breast cancer is described. The method may comprise developing a genetic profile from marker genes from a breast tissue sample; and identifying a breast cancer patient as likely to respond to a treatment for breast cancer if the expression profile matches a predetermined expression profile that indicates that a patient will respond to the treatment. In another embodiment, the marker genes may comprise ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof.

In another embodiment, treatment for breast cancer may comprise a chemotherapeutic agent, radiation and a combination thereof. In another embodiment, the chemotherapeutic agent comprises alkylating agents, antimetabolites, anthracyclines, anti-tumor inhibitors, topoisomerase I inhibitors, topoisomerase II inhibitors, corticosteroids and combinations thereof.

In a preferred embodiment, the therapeutic agent is Docetaxel. In yet another embodiment, chemotherapy is provided to the patients after gene expression profiling.

In another embodiment, a method for predicting the efficacy of treatment of breast cancer comprising is provided. The method may comprise developing an expression profile from marker genes from a cancerous breast tissue sample, normalizing the expression level of each marker gene to the mean expression level of that gene for a plurality of samples as a predetermined expression profile level, normalizing each expression profile to the median gene expression level of the plurality of marker genes, and predicting the efficacy of treatment if the expression profile from the cancerous breast tissue matches the predetermined expression profile. In another embodiment, the marker gene may comprise ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, ODC1 and combinations thereof.

In yet another embodiment, the expression profile of cancerous breast tissue "matches" the predetermined expression profile, if the quantity and quality of breast tumor tissue is sufficient such that hierarchical cluster analysis achieves a separation into two clusters with significantly more Responsive Patients in one cluster and significantly more Non-responsive Patients in the other cluster, such that the statistical significance is $p<0.05$ by using a ROC test.

In yet another embodiment, a match is determined by comparing Pearson product moment correlation coefficients between the normalized profile of the cancerous breast tissue and all pre-existing profiles and further identifying the best match (the highest correlation coefficient). If the preexisting match is in the Responsive cluster, the new patient (sample) is predicted to respond to chemotherapy. If the preexisting match is in the Non-responsive group, the new patient is predicted to be non-responsive to chemotherapy.

What is claimed is:

1. A method of treating a human subject with breast cancer with a taxane, wherein the taxane has been identified as being predicted to be efficacious for the human subject, the method comprising:

measuring RNA expression from a human breast cancer tissue sample by using a microarray or amplification process of a set of genes consisting of ASPM, NCAPG, CDKN3, AURKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, and ODC1 to produce an RNA expression profile of the set of genes;

performing hierarchical clustered analysis on the produced RNA expression profile from the human breast cancer tissue to a hierarchical clustered dataset comprising patients that have responded to the taxane, wherein the hierarchical clustered dataset is a gene expression profile set consisting of ASPM, NCAPG, CDKN3, AEIRKA, FOXM1, CEP55, TNFRSF6B, FGFBP1, CAPRIN2, TUBG1, ZWILCH, RRM2, ACTB, ACTN1, EPHA2, TRIP13, CKS2, VRK1, DUSP4, EIF4A1, SERPINE2, and ODC1;

predicting that the taxane will be efficacious for the subject if the RNA expression profile from the human breast cancer tissue sample matches the hierarchical clustered dataset comprising patients that have responded to a taxane; and administering a therapeutically effective amount of the taxane to the human subject that has been identified as being predicted to be efficacious for taxane treatment.

2. The method of claim 1, further comprising administering radiation to the subject.

3. The method of claim 1, further comprising administering an alkylating agent, an antimetabolite, an anthracycline, an anti-mitotic agent, a topoisomerase I inhibitor, a topoisomerase II inhibitor, a corticosteroid or any combination thereof.

4. The method of claim 1, further comprising generating a report indicating the efficacy of the treatment.

5. The method of claim 1 wherein the taxane is docetaxel.

6. The method of claim 1 wherein the taxane is paclitaxel.

7. The method of claim 1, further comprising obtaining a breast cancer tissue sample from the subject.

8. The method of claim 1, wherein the amplifying step comprises performing PCR.

9. The method of claim 1, wherein the breast cancer is negative for expression of estrogen receptor, progesterone receptor and HER2/neu (erbb2) receptor.

10. The method of claim 1, wherein the breast cancer is positive for expression of estrogen receptor.

* * * * *